United States Patent [19]
Määttä et al.

[11] Patent Number: 5,849,886
[45] Date of Patent: Dec. 15, 1998

[54] EXTRACTION OF MYELIN BASIC PROTEIN

[75] Inventors: Jorma Määttä; Ari Hinkkanen, both of Turku, Finland

[73] Assignee: OY Aboatech AB, Turku, Finland

[21] Appl. No.: 677,466

[22] Filed: Jul. 10, 1996

[51] Int. Cl.$^6$ .............................. A23J 1/00; C07K 1/00; A01N 37/10; A61K 31/19
[52] U.S. Cl. .................. 530/426; 530/412; 530/423; 530/839; 530/417; 514/570
[58] Field of Search ................... 530/417, 839, 530/426, 412, 423; 514/570

[56] References Cited

FOREIGN PATENT DOCUMENTS

WO 91 12816  9/1991  WIPO .

OTHER PUBLICATIONS

Raziuddin S., et al. "Experimental Allergic Encephalomyelitis In Lewis Rats: Inhibition By Bacterial Lipopolysaccharides and Acquired Resistance to Reinduction by Challenge With Myelin Basic Protein", *Journal of Immunology*, vol. 127, No. 1, Jul. 1981, pp. 16–20.
Chou et al., "Monoclonal Antibodies To Hyman Myelin Basic Protein", *Journal of Neurochemistry*, vol. 46, No. 1, 1 Jan. 1986, pp. 47–53.
Voskuhl R. R. et al., "T–lymphocyte Recognition of a Portion of Myelin Basic Protein Encoded by an Exon Expressed During Myelination", *Journal of Neuroimmunology*, vol. 42, 1993, pp. 187–192.
Määttä J. A. et al., "Detection of Myelin Basic Protein Isoforms by Organic Concentration", Biochem. Biophys. Res. Commun., vol. 238, No. 2, 1997 USA, pp. 489–502 (abstract).
European Search Report dated 10 Nov. 1997, three pages.
Martenson et al., "Extraction of rat myelin basic protein free of other basic proteins of whole central nervous system tissue; an analysis of its electrophoretic heterogeneity", *Chemical Abstracts*, vol. 71, p. 26, abstract No. 56711K (1969).
Deibler et al., "Large Scale Preparation of Myelin Basic Protein From Central Nervous Tissue of Several Mammalian Species", *Preparative Biochemistry*, pp. 139–165 (1972).
Eylar et al., "Myelin Basic Proteins", *Isolation of Selected Membrane Components*, pp. 323–341 (1974).

de Ferra et al., "Alternative Splicing Accounts for the Four Forms of Myelin Basic Protein", *Cell*, vol. 43, pp. 721–727 (Dec. 1985).
Bellini et al., "A Rapid Method for Purification of Myelin Basic Protein", *Journal of Neurochemistry*, vol. 46, No. 5, pp. 1644–1646 (1986).
Geigerich et al., "Rapid method based on reversed–phase high–performance liquid chromotography for purification of human myelin basic protein and its thrombic and endoproteinase Lys–C peptides", *Journal of Chromotography*, vol. 528, pp. 79–90 (1990).
Nakajima et al., "Novel Isoforms of Mouse Myelin Basic Protein Predominantly Expressed in Embryonic Stage", *Journal of Neurochemistry*, vol. 60, No. 4, pp. 1554–1563 (1993).
Eylar, EH et al. 1974. Methods. Enzymol. 32:323–341, 1974.
Riccio, P. et al. Mol. Chem. Neuro Pathol. 13(3):185–94, 1990.
Cochary, EF. et al. J. Neurochemistry 55(2):602–610, 1990.
Fannon, Am et al. Neuroreport 2(3):135–8, 1991.
Bonlias, C. et al. 1995. Arch. Biochem. Biophys. 322(1):174–82, 1995.
O. M. Pitts et al., "An Evaluation of a Procedure for the Isolation of Myelin Basic Protein (BP)," pp. 239–264, Preparative Biochemistry 6(4) (1976).

*Primary Examiner*—Lila Feisee
*Assistant Examiner*—Lin Sun-Hoffman
*Attorney, Agent, or Firm*—Marshall, O'Toole, Gerstein, Murray & Borun

[57] ABSTRACT

A process for extraction of myelin basic protein from myelin containing tissue, such as central nervous system tissue, which process comprises the following steps:
  extraction of the myelin basic protein from myelin containing tissue with an organic solvent selected from the group consisting of chloroform and compounds having a polarity similar to that of chloroform;
  incubation of the organic phase in the presence of a lower aliphatic alcohol or propylene glycol;
  transfer of the myelin basic protein from the lower aliphatic alcohol/organic solvent mixture to an aqueous phase with the aid of hydrogen ions (protons); and
  recovery of the purified myelin basic protein. The invention also relates to the product obtainable by the process.

12 Claims, 8 Drawing Sheets

EXTRACTION OF MYELIN BASIC PROTEIN

FIELD OF THE INVENTION

The present invention relates to a process for extraction of myelin basic protein from myelin containing tissue, such as central nervous system tissue, which process produces highly purified myelin basic protein in a short time. The protein product recovered includes, in addition to the major myelin basic protein isoforms, also several minor isoforms not generally obtained by other methods (Mastronardi, F. G. et al., *J. Neurochem.* (1993) 60, 153–160).

BACKGROUND OF THE INVENTION

Myelin is a unique multilamellar membrane structure that surrounds and electrically insulates axons to facilitate the conduction of neuronal impulses. This elaborate structure is synthesized and assembled by oligodendrocytes in the central nervous system (CNS) and by Schwann cells in the peripheral nervous system (PNS) (de Ferra, F. et al., *Cell* 43, Part 2, (1985) 721–727; Nakajima, K. et al., *J. Neurochemistry*, 60 (1993) 1554–1563). Myelin basic protein (MBP) is one of the major constituents of the central nervous system myelin, since it constitutes approximately 30% of its myelin proteins.

Mouse MBP is known to have at least four isoforms as translated proteins (Barbarese, E. et al., *Proc Natl. Acad. Sci. USA*, 74 (1977) 3360–3364). The molecular weight of these proteins are 21.5, 18.5, 17 and 14 kDa. Recently separate mRNAs for 21.5, 20.2, 18.5, 17 (two isoforms), one isoform between 17 an 14 kDa and under 14 kDa have been reported (see FIG. 3 in reference Nakajima, K. et al., ibid.).

Experimental allergic encephalomyelitis (EAE) is a widely used animal model for multiple sclerosis (MS), where MBP is considered one putative autoantigen. EAE can be induced in rodents by immunizing the animals with MBP in strong adjuvant. On the other hand, oral administration of pure MBP is shown to tolerize animals for MBP inhibiting EAE induction (Miller, A. et al., *FASEB*, 5 (1991) 2569–2566; Miller, A. et al., *Pros Natl. Acad. Sci USA*, 89 (1992) 421–425). In the USA, trials are ongoing where bovine MBP is orally administered to MS patients (Weiner and Hafler, unpublished). Further, MBP may be involved in the pathogenesis of other neurological disorders (Carnegie P. R. and Moore, Proteins of the Nervous System, Raven Press (1980) 2nd ed. pp. 119–143).

Several methods for the purification of MBP have been established. Most of them are based on primary extraction of lipids from the brain tissue with subsequent separation of major myelin basic protein isoform or isoforms from other components soluble in aqueous buffers (Deibler G. E. et al., *Prep. Biochem.*, 2 (1971) 139–165; Eylar E. H. et al., *Methods Enzymol.*, 32 (1974) 323–341; Bellini, T. et al., *J. Neurochemistry*, 46 (1986) 1644–1646; Giegerich, G. et al., *J. Chromatogr.*, 528 (1990) 79–90). Also extraction using detergents has been reported (Riccio, P. et al., *Mol. Chem. Neuropathol.*, 13 (1990) 185–194). Detergents, in general, inhibit immunological assays. Common to all the methods is that they include multiple steps of extraction of lipids followed by separations of the remaining proteins using different chromatographic steps. These are time consuming and hence expose MBP to proteolytic degradation, which is known to be active in central nervous system tissue due to high activities of neutral and acidic proteases.

Most widely used processes (Eylar, E. H. et al., ibid.; Deibler, G. E. et al., ibid.) start with the extraction of MBP containing tissue with a chloroform-methanol mixture, which renders MBP water soluble. Hence the MBP is among a variety of other CNS proteins, from which it has to be separated.

In one known purification process, MBP was purified from insoluble material from chloroform-methanol and acetone treated CNS tissue or sucrose gradient isolated myelin from rat brain or spinal cord. The remnants from solvent treatments or purified myelin were washed with pH 3.0 water, and MBP was extracted from the debris with 0.1M HCl (Martenson, R. E., *J. Biol. Chem.*, 244(16) (1969) 4268–4272). That study confirmed earlier observations that rat MBP consists of multiple electrophoretic forms.

In another known purification procedure of MBP, extracts of canine and porcine brain were treated in a sequential manner with chloroform-methanol (2:1 v/v), acetone, and deionised water (Pitts, O. M. et al., Prep. Biochem. (USA), 06(04) (1976) 239–164). This was followed by a precipitation of the extract at pH 9.0, and gel filtration of the supernatant in dilute hydrochloric acid.

None of these processes mentioned above results in the simultaneous purification of different MBP isoforms in the brain, as does the process of the present invention. Some of these isoforms are implicated as potential autoantigens in multiple sclerosis (MS) (Voskuhl, R. R. et al., *J. Neuroimmunology*, 42 (1993) 187–192; Voskuhl, R. R. et al., *J. Immunology*, 153 (1994) 4834–4844).

According to the present invention a simple extraction procedure has been developed which produces highly purified MBP in a short time. The protein product according to the process includes, in addition to the major MBP isoforms, also several minor isoformic myelin basic proteins not generally obtained by prior processes. Moreover, isoforms only predicted on the basis of presence of mRNA in the central nervous system tissue (Nakajima, K. et al., *J. Neurochemistry*, 60 (1993) 1554–1563) can be detected in the myelin basic protein prepared according to our invention when analysed with specific antiserum.

SUMMARY OF THE INVENTION

The object of the present invention is thus a process for extraction of myelin basic protein from myelin containing tissue, such as central nervous system tissue, which process comprises the following steps:

extraction of the myelin basic protein from the myelin containing tissue with an organic solvent selected from the group consisting of chloroform and compounds having a polarity similar to that of chloroform;

incubation of the organic phase in the presence of a lower aliphatic alcohol or propylene glycol;

transfer of the myelin basic protein from the organic phase into an aqueous phase with the aid of hydrogen ions (protons); and recovery of the purified myelin basic proteins.

REFERENCE TO THE DRAWING

In the appended figures, the coomassie stainings were made to 0.75 mm thick SDS-PAGE minigel when 4 µg proteins according to Bradford analysis is used as a sample. Similar gels were run for immunoblot analysis. Proteins were electro-transferred onto nitrocellulose filters. Polyclonal anti guinea-pig MBP serum raised in rabbit by guinea-pig MBP purified by the method of Eylar et al. (1971, ibid.) was used as primary antibody. Horseradish peroxidase-conjugated goat anti rabbit IgG conjugate was used as secondary antibody. Immunoreactions were visualized by enhanced chemiluminescence (Amersham).

FIG. 1 shows at A) coomassie staining of the final myelin basic protein product from various species and at B) and C) immunoblot of similar gel (15 second and 40 second exposures during enhanced chemiluminescence, respectively). Lane 1, Promega low molecular weight marker; lane 2, bovine MBP; lane 3, human MBP; lane 4, porcine MBP; lane 5, rabbit MBP; lane 6, chicken MBP; lane 7, guinea-pig MBP; lane 8, rat MBP; lane 9, mouse MBP; lane 10, fish (Lota lota) MBP.

FIG. 2: MBP isoforms visualized with coomassie staining (A) or immunoblot detected with enhanced chemiluminescence (B). Lane st, Promega medium range, molecular weight marker; lane 1, mouse brain homogenate (500 μg); lane 2, MBP from mouse brain (8 μg); lane 3, spinal cord homogenate (500 μg); lane 4, MBP from mouse spinal cord (5 μg). The exonic elements in mRNAs corresponding to the distinct isoforms are drawn according to Nakajima et al. (1993). Note that the relative mobility of MBPs is reduced compared to standard proteins of similar size.

In FIG. 3 matrix-assisted laser desorption mass spectrometry (LASERMAT) results for A) mouse and B) human MBP is presented. The analysis was performed in a Finnigan-MAT apparatus using 100 pmol protein sample mixed into sinapinic acid. For human MBP, the m+2H$^+$peak (9.3 kDa) is also visible.

FIG. 4 shows peptide-grade SDS-PAGE analysis of the product. The analysis was performed for human and mouse MBP by a Pharmacia Phast System machine. A: coomassie staining, B: immunoblot analysis. Lane 1, human MBP; lane 2, mouse MBP; lane 3, guinea-pig MBP digested partially by thrombin. The two major bands in the thrombin digest have molecular weights of 10.5 kDa and 8 kDa. Using 3 min illumination in chemiluminescence reaction detection (Amersham), no stainable or immunoreactive low molecular weight degradation products can be observed.

FIG. 5. Effect of the wash of the organic phase with neutral water. A: coomassie staining, B: immunoblot analysis. Lane 1, wash water phase; lane 2, final product when organic phase was washed with neutral water; lane 3, final product without wash. The washed proteins constitute about 2–5% of the proteins in the organic phase.

FIG. 6: Stability of the product. Lane 1, frozen lyophilized product; lane 2, product kept one week in water solution at room temperature; lane 3, product kept one week at +4° C. All MBP samples were made from porcine brain.

FIG. 7. MBP products made from mouse brain kept at +4° C. post mortem. Lane 1, fresh brain; lane 2, 4 h incubation; lane 3, 1 day incubation; lane 4, 4 days incubation; lane 5, 8 days incubation.

DETAILED DESCRIPTION OF THE INVENTION

Figure 1A:
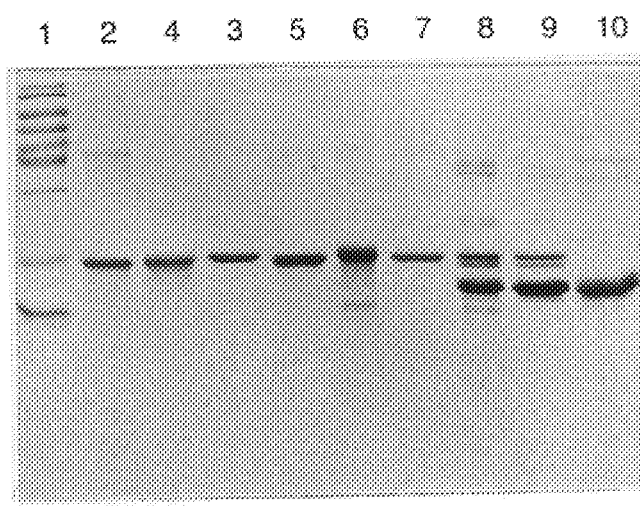

The process according to the invention is based on the extraction of myelin containing tissue such as brain tissue with an excess of organic solvent. Thus the myelin basic protein isoforms are almost exclusively transferred into the organic solvent.

By the term "myelin containing tissue" is meant such as that of the central nervous system and the peripheral nervous system. The tissue can be fresh or frozen.

The term "organic solvent" means in this context an organic solvent having a polarity similar to that of chloroform ($E^2Al_2O_3$ =0.38 –0.42), such as chloroform, methylene chloride and diethylether.

The ratio of organic solvent to tissue is not critical, but a preferred range is 3 to 8 ml organic solvent per 1 g myelin containing tissue. In a preferred embodiment, chloroform is used in ratio of a total of 7.5 ml solvent—in 5 ml and 2.5 ml batches—per 1 g myelin containing tissue.

This means that pro each mg of pure myelin basic protein about 1.5 ml (spinal cord) to 5 ml (frozen brain) organic solvent is used. Preliminary analysis show that the organic solvent can be recycled, i.e. the organic solvent fraction, which has already been used to extract myelin basic proteins, can be used to extract more of it from another sample of myelin containing tissue. After extraction, the organic phase is preferably washed with neutral water in order to remove proteins soluble at neutral pH. Such proteins constitute generally about 2 to 5% of the proteins carried in the organic phase.

In the next step of the process the myelin basic protein isoforms extracted into the organic solvent are made water soluble. This is done using a lower aliphatic alcohol or propylene glycol and hydrogen ions. The organic phase is incubated at room temperature in the presence of a lower aliphatic alcohol or propylene glycol. The preferred range of lower aliphatic alcohol or propylene glycol is 1 ml per 2 ml organic solvent containing myelin basic protein. This step is essential to render the myelin basic protein in the organic phase transferrable to the aqueous phase.

In this context, by the term "lower aliphatic alcohol" is meant the following alcohols:

| alcohol | yield |
| --- | --- |
| methanol | +++ |
| ethanol | +++ |
| propanol | +++ |
| 2-propanol | +++ |
| butanol | ++ |
| 2-butanol | ++ |
| iso-amyl alcohol | + |
| tert-amyl alcohol | ++ |

In addition, the yield by propylene glycol is comparable to that obtained by methanol.

After incubation with lower aliphatic alcohol/propylene glycol, the myelin basic protein isoforms are quantitatively transferred from the mixture of organic solvent and lower aliphatic alcohol/propylene glycol into acidic water, which is preferably used in a ratio of 1 ml water per 6 ml of mixture of organic solvent and lower aliphatic alcohol/propylene glycol. Hydrogen ions (protons) are used to carry myelin basic proteins into the aqueous phase by acidifying the aqueous phase with for example hydrochloric acid. As long as the organic solvent containing myelin basic protein has buffering capacity so that the pH of the acidified aqueous phase rises when mixed with the mixture of organic solvent and lower aliphatic alcohol/propylene glycol, more myelin basic protein can be transferred from the mixture of organic solvent and lower aliphatic alcohol/propylene glycol into the aqueous phase. The pH is kept preferrably at about 2. From the aqueos phase thus obtained the myelin basic proteins are recovered. This can take place, for example, by freeze-drying the product twice or gel filtration and freeze-drying. According to a preferred embodiment, the product is gel filtrated and freeze dried.

During the purification process of the present invention myelin basic protein most probably locates itself immediately into the organic phase. This results in that the degree of possible proteolysis of the myelin basic protein is minimized.

Although it is still unknown if the myelin basic protein is present in the organic solvent in soluble form, or in the form of lipid-associated micelles, we have indicated by thin layer chromatography that the myelin basic protein is lipid-bound in the lyophilized preparate. The nature of this (these) lipid(s) is not known.

The invention will now be described in more detail below by means of an example.

EXAMPLE

Preparation of the myelin basic protein product 3.08 g frozen mouse brain was homogenized into 15 ml of chloroform at room temperature (RT) with a Sorvall Omni-Mixer 17220 homogenizer using four 30 second bursts at full speed intervened by 30 second pauses to avoid excess heating. The organic phase was separated from tissue debris and intracellular/cytosolic fluid by centrifugating 5 min 4500 rcf at RT with a Sorvall SA-600 rotor. The intracellular/cytosolic fluid was discarded and the debris was re-extracted with 7.5 ml chloroform using two bursts in the homogenizer and the organic phase was separated as before. The chloroform fractions were pooled and the volume was measured to be 18.2 ml.

The organic phase was washed in a 50 ml conical tube by adding 4.5 ml neutral water and vortexing gently for 15 seconds. The water phase was separated by centrifugating 5 minutes 2000 rpm with a Sorvall H5094 rotor at RT. The water phase was carefully removed from the top of the organic phase.

To the chloroform phase 9 ml methanol was added and the mixture was vortexed for 30 seconds. Then, 4.5 ml water and 120 µl 1M HCl was added. The mixture was vortexed and the pH of the separating aqueous phase was checked periodically by Acilit (Merck) pH paper. As long as the pH arose during vortexing, more 1M HCl was added. After adding 140 µl 1M HCl, the pH of the aqueous phase remained 1.5–2.0.

The acid aqueous phase was separated from the organic phase by centrifugating 10 min at 2000 rpm with a Sorvall H5094 rotor at RT. Total 9 ml of acid aqueous phase was recovered, concentratred to 3 ml in a Büchi Rotavapor vacuum concentrator, gel filtrated in a Pharmacia PD-10 column and lyophilized. The final product appeared as a white powder and the total yield of protein was 4.3 mg according to Bradford analysis.

Analysis of the myelin basic proteins obtained by the method

Using 4 µg protein samples from various species all proteins visible in the coomassie stained 0.75 mm thick SDS-PAGE react with the polyclonal myelin basic protein specific antiserum. The serum was raised in rabbits by immunizing with guinea-pig myelin basic protein purified by the method of Eylar et al. (1974).

Figure 1B:
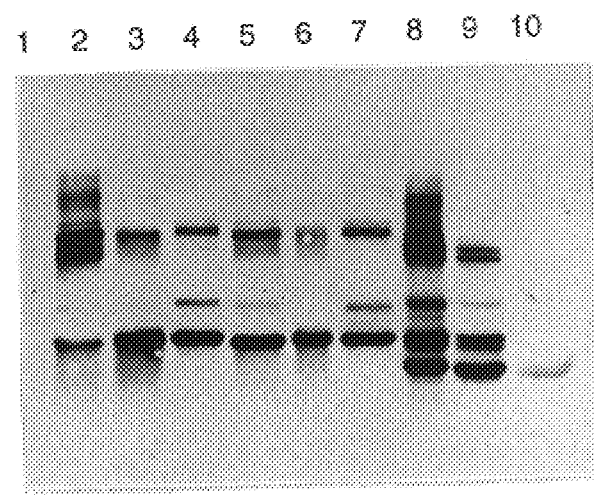

Immunoreactive bands corresponding to nearly all isoforms predicted for mouse by mRNA analysis, but not analyzed for other species could be detected in all mammalian myelin basic protein samples tested (See FIG. 1A, B and C and Table 1). Moreover, immunoreactive bands are also detected, which are not visible in coomassie staining but the size of which agrees with the predicted myelin basic protein isoform size determined by mRNA analysis (See FIG. 1 and Table 1).

Figure 2A:
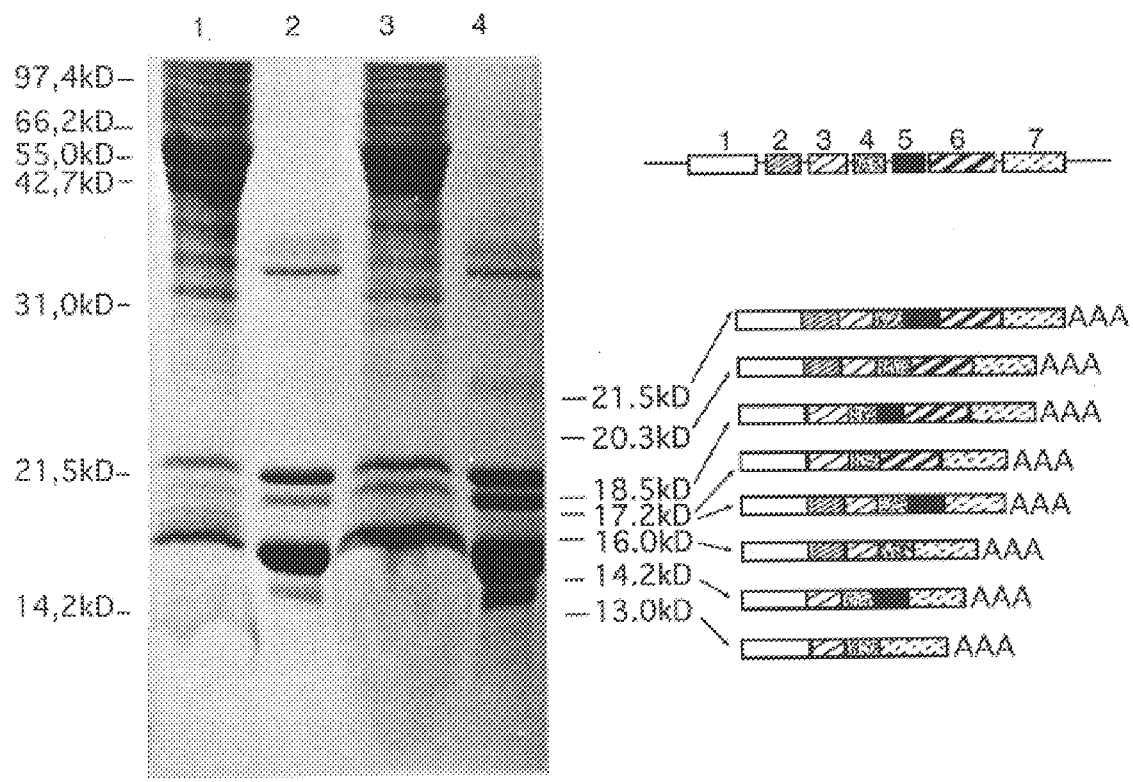
Figure 2B:
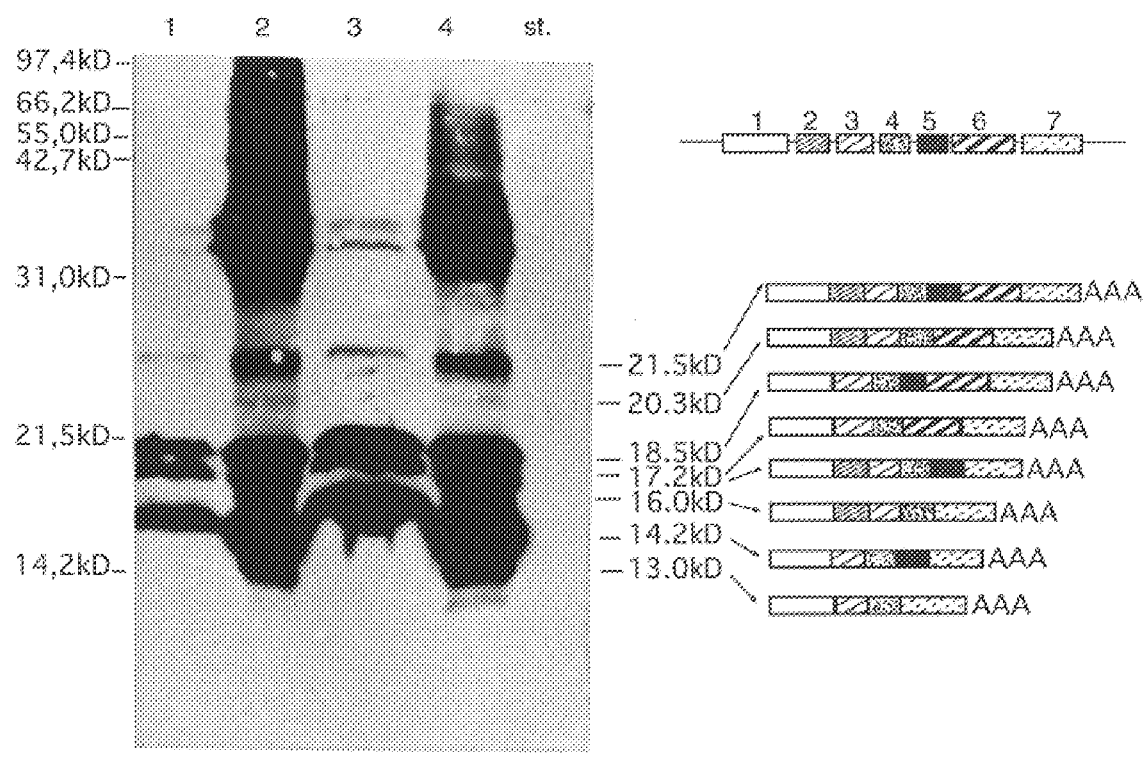

All MBP isoforms detected in brain and spinal cord homogenates were also present in the final product (FIG. 2).

Purity and solubility of the product

Figure 3:
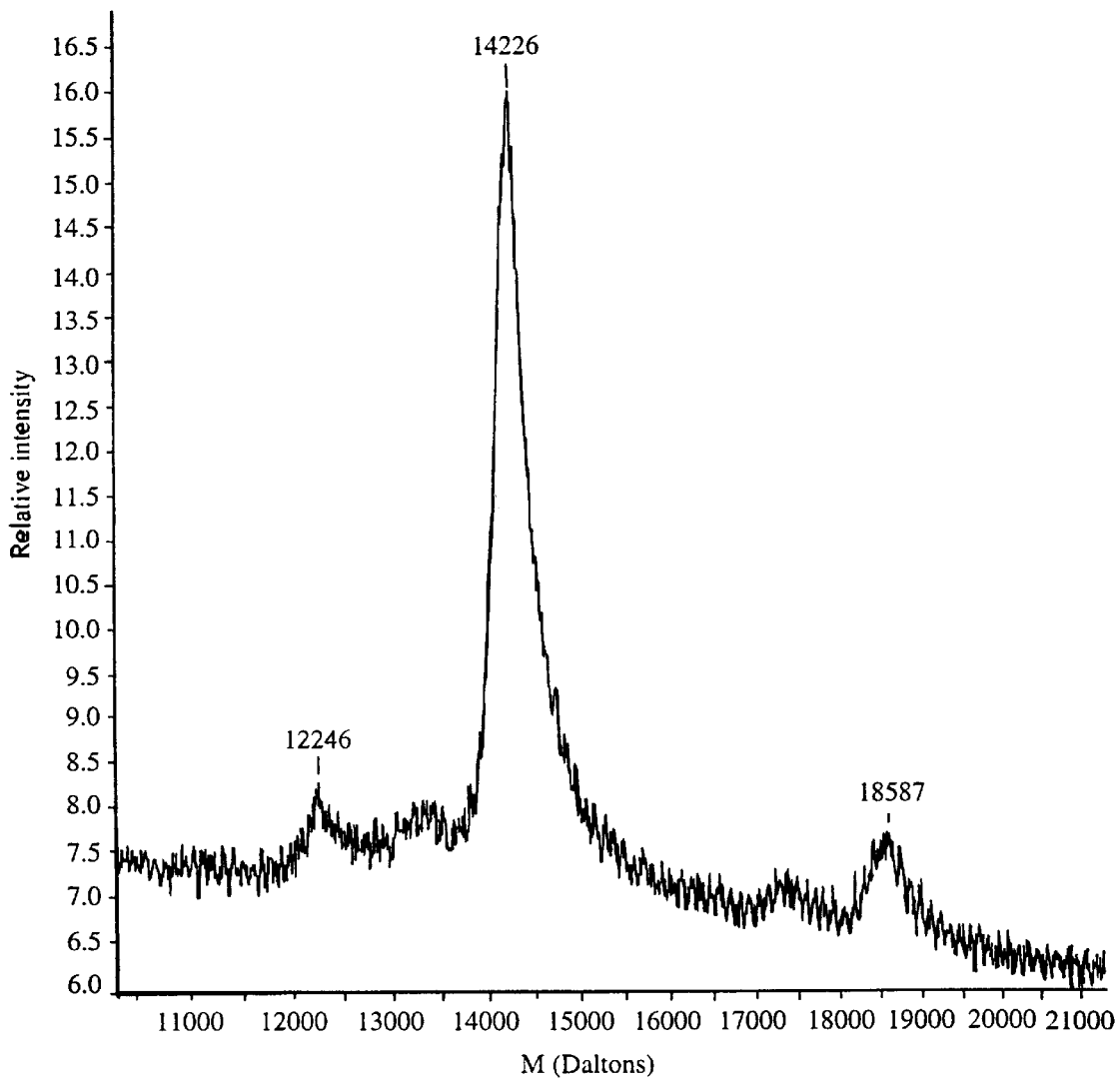
Figure 3:
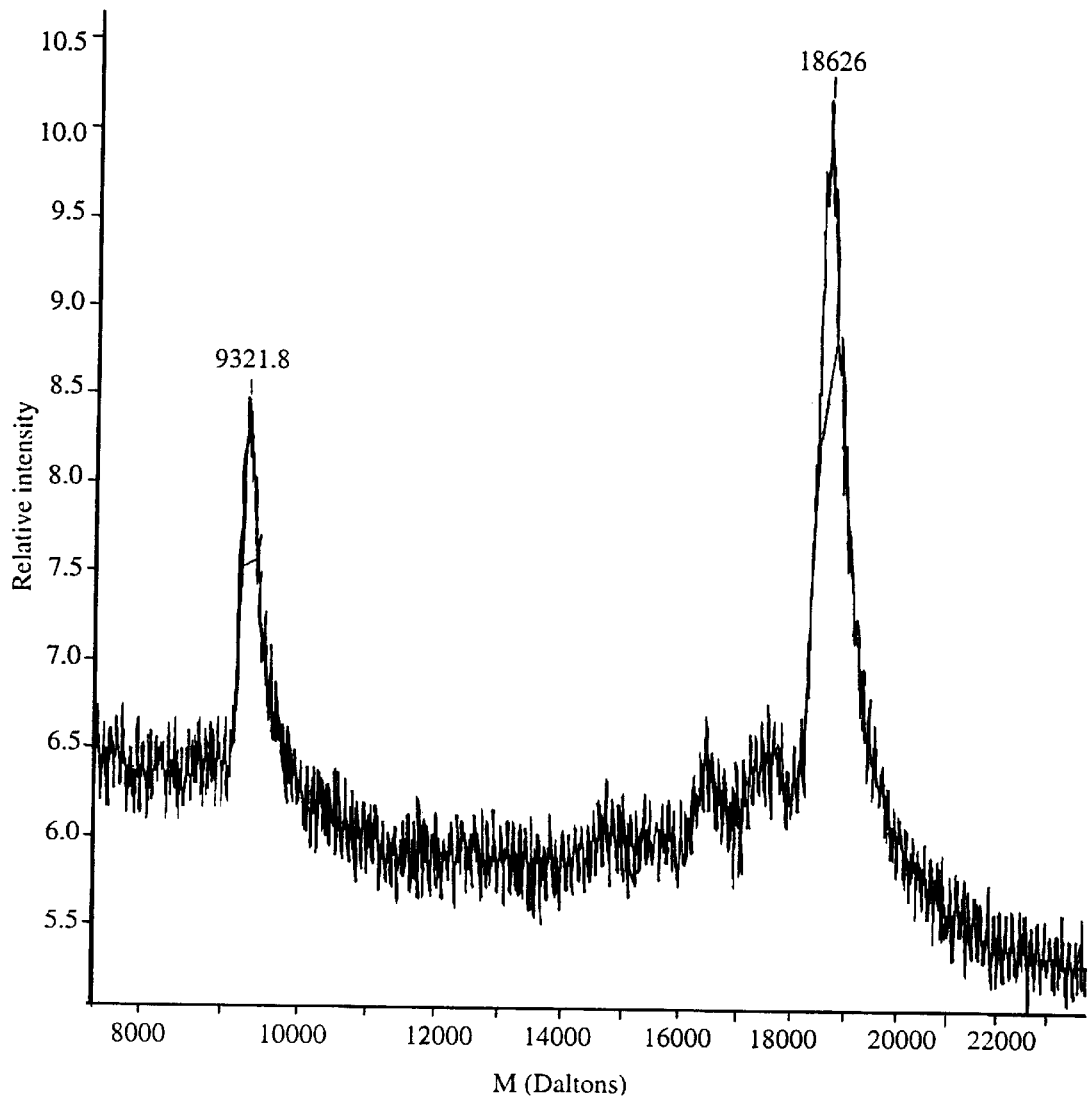
Figure 4A:
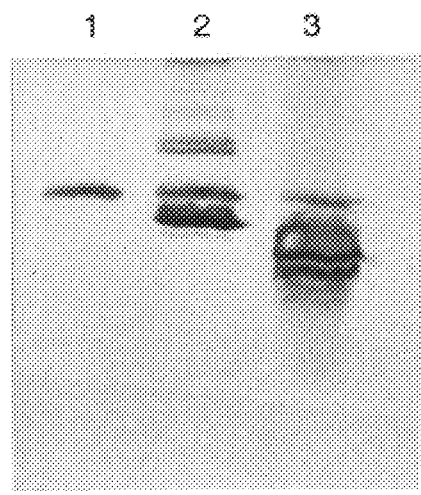
Figure 4B:
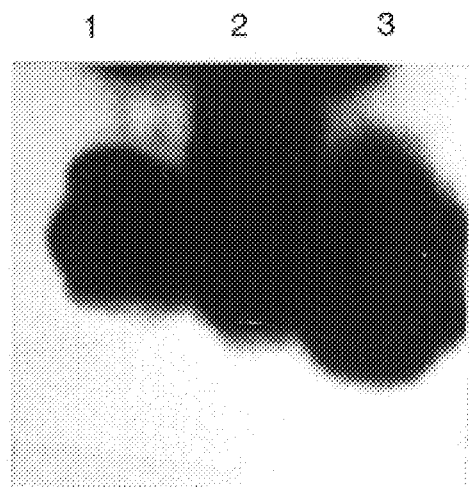

The final myelin basic protein preparation is readily soluble in aqueous solvents such as distilled water and phosphate buffered saline (PBS). After two lyophilisations or gel filtration and lyophilisation, the protein appears as a white powder. No contaminating proteins were detected by coomassie staining, reversed-phase high-performance liquid-chromatography (RP-HPLC) or immunoblot analysis. Molecular weight analysis by matrix-assisted laser-desorption mass spectrometry (LASERMAT) of the myelin basic protein preparations from human and mouse showed that at least the molecular weights of the major isoforms (only the weights of the major isoforms were measureable by LASERMAT) corresponded to those predicted from mRNA, confirming that at least those isoforms are nondegraded (See FIG. 3). Peptide grade SDS-PAGE analysis by Pharmacia Phast System revealed no bands below approximately 10 kDa, further supporting that the protein products are intact (See FIG. 4). Also a partial thrombin digestion (Law, M. J., et al., *J. Neurochem.*,42 (1984) 559–568) of the myelin basic protein preparation results in the typical peptide pattern.

Figure 5A:
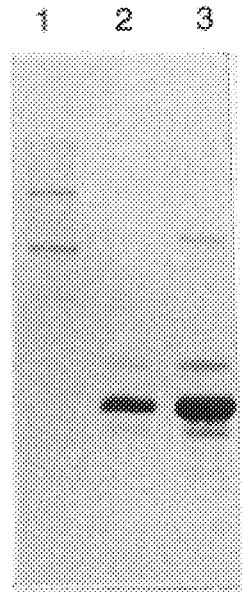
Figure 5B:

The importance of neutral water wash to the organic phase is not clear as no difference in the protein content of the final product could be demonstrated, whether the organic phase is washed or not. However minor amounts of proteins nonrelated to myelin basic proteins could be seen in the water phase used to wash the organic phase (See FIG. 5).

Yield

One gram fresh brain yields about 1.5 (frozen brain) to 5 milligrams (spinal cord) a highly purified myelin basic protein isoform mixture. The yield is in same range as obtained by other published methods (see Table 2).

The extraction of myelin basic protein seems to function equally with all species tested (see FIG. 1 and Table 1), and both brain and spinal cord tissue (FIG. 2) are suitable raw materials for purification of myelin basic protein from the central nervous system. The method is also suitable for purification of myelin basic protein from the peripheral nervous system.

Isoforms

The best characterized species for myelin basic protein mRNA expression is mouse. Detected messenger RNAs of mouse myelin basic protein encode 13.0, 14.2, 16.0, 17 (two isoforms) ,18.5, 20.2, and 21.5 kDa polypeptides (deFerra, F. et al., 1985, ibid.; Nakajima, K. et al.,1993, ibid.). A protein corresponding to the 21.5 kDa and 16 kDa myelin basic protein isoforms are present in preparations from each species except fish. For human the 21.5 kDa isoform, now detected in the purified preparate by immunoreaction (FIG. 1C, lane 3), has only been predicted by mRNA analysis from myelinating and remyelinating brain tissue (Kamholz, J. et al., (1986) *Proc. Natl. Acad. Sci. USA* 83, 4962–4966). The 16 kDa isoform present also in human myelin basic protein preparate has not—according to the literature—been predicted for human by mRNA analysis. These isoforms contain an amino acid sequence encoded by exon-2 of the myelin basic protein gene. This region of MBP has shown to be recognized by myelin basic protein specific T cell lines from MS patients (Voskuhl, R. R. et al., (1993), ibid.), thus possibly being of key importance when myelin basic protein tolerisation treatments are planned for MS patients. These exon-2 containing isoforms were present in substantial amounts in porcine and bovine myelin basic protein preparates—species suitable as a source of large scale myelin basic protein purification.

Figure 1C:
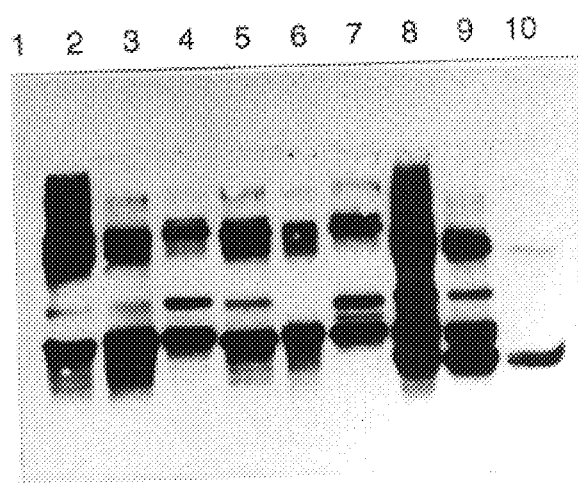

The 14.2 kDa band representing the major polypeptide for mouse MBP and rat MBP was present also in all other species. Messenger RNA encoding for an approximately 13 kDa isoform was recently detected for mMBP (Mathisen, P. M., et al. (1993) *Proc. Natl. Aca. Sci. USA* 90, 10125–10129). A protein of corresponding size was recognized by the MBP-specific antiserum in extracted mouse and rat samples and weakly also in other mammalian species after prolonged exposure (FIG. 1C). Additionally in rMBP and mMBP an approximately 10 kDa polypeptide became visible in immunoreaction (FIG. 1C, lanes 8, 9).

Stability

Figure 6:
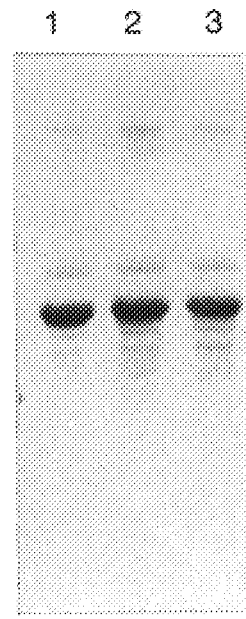

The myelin basic protein preparate is stable as a powder at −20° C. for at least two years. In aqueous solution, after storage for one week at room temperature or at +4° C., no degradation was observed with coomassie staining or immunodetection (FIG. 6). The stability may result from high selectivity on transfer of myelin basic proteins into the organic phase and further into the aqueous phase and the denaturing effect of chloroform and acid pH for proteases.

Figure 7:
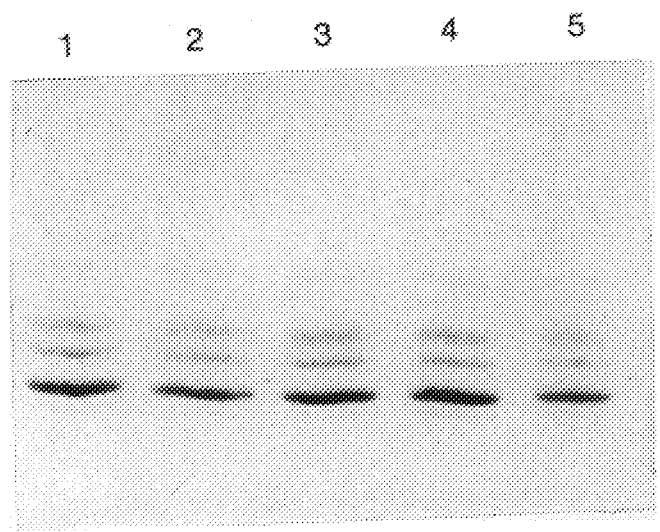

We found out that myelin basic proteins can still be extracted in substantial quantities from brain stored for one week at +4° C. (see FIG. 7). Hence, no expensive deep freeze chain is needed for raw material handling and transport. Once the tissue has been frozen and thawed, the myelin protein yields are markedly lowered.

Time considerations and scalability

In laboratory scale, meaning in this context purification of myelin basic protein from 100 mg to 100 g CNS tissue, the time required from beginning of the purification from tissue to a preparate ready for lyophilisation is approximately three hours. This is remarkably faster compared to the one day when using the shortest published method (Bellini et al., ibid.) and to 5 days by the commonly used methods of Deibler G. E. et al., (1971) and Eylar E. H. et al., (1974).

So far the method has been shown to function for small tissue samples of 100 mg to preparative laboratory scale using 100 g of tissue as a starting material. No reason to inhibit scaling the method for large industrial scale has occured.

Uses

The myelin protein product has been shown to function as a substrate for protein kinases, one of the potential uses of myelin basic proteins (Yang, S. D. et al., *J. Biol. Chem.*, 269 (1994) 29855–29859; Moriyama, T., et al., *FEBS Lett.*, 353 (1994) 305–308). Moreover we have shown that this myelin basic protein product can be used in immunospot assays and T cell proliferation assays for the detection of the presence of antigen-specific T lymphocytes. The myelin basic protein product was shown to be effective also in induction of EAE in SJL mice.

In accordance with the afore mentioned, the myelin basic protein product of the present invention can be used for immunological studies which aim at understanding the pathogenesis of inflammatory demyelinating diseases, such as multiple sclerosis, in humans, and probably at the development of treatments of these diseases by oral tolerization.

TABLE 1

Expression of MBP isoforms in CNS of different species

| | Molecular weight, kDa | | | | | | |
|---|---|---|---|---|---|---|---|
| Species | 21.5 | 20.2 | 18.5 | 17.2* | 16.0 | 14.2 | 13 | 10 |
| Mouse | ++ | + | +++ | +++ | ++ | ++++ | +++ | + |
| Rat | ++ | + | ++++ | +++ | ++ | ++++ | +++ | ++ |
| G-pig | ++ | + | ++++ | + | + | + | + | − |
| Rabbit | + | − | ++++ | + | + | + | + | − |
| Chicken | − | − | ++++ | ++ | ++ | +++ | | ° |
| Human | + | − | ++++ | +++ | +++ | ++ | + | − |
| Bovine | +++ | + | ++++ | +++ | ++ | + | + | − |
| Swine | +++ | + | ++++ | +++ | ++ | | | |
| Fish# | − | − | − | − | − | ++++ | +++ | − |

*The 17.2 kDa form consists of two closely migrating forms
The 14.0 kDa form appeared as a duplicate, and an approximately 10 kDa band was visible in coomassie staining but not in immunoblot (see FIG. 1).
°Band visible in coomassie staining, but not recognized by the polyclonal anti guinea-pig MBP serum.
(−) not detected; (+) visible in immunoblot after extended exposure; (++) visible in immunoblot but not in coomassie staining; (+++) visible both in coomassie and immunostaining; (++++), strong coomassie and immunostaining.

TABLE 2

Yield of MBP and isolation time in laboratory scale before lyophilization when using various methods

| Method | Yield mg/g | Time | Source |
|---|---|---|---|
| Present invention | 2.8 | 3 h | fresh porcine brain |
| | 1.4 | 3 h | frozen porcine brain |
| | 1.4 | 3 h | frozen mouse brain |
| | 5.5 | 3 h | frozen mouse spinal cord |
| Bellini et al. | 6.7 | 1 d | fresh bovine white matter |
| Deibler et al. | 1.83 | 5 d | frozen guinea pig brain |
| | 5.56 | 5 d | frozen guinea pig spinal cord |
| Giegerich et al. | 1.65 | 2 d | frozen human brain |

We claim:

1. Process for extracting myelin basic protein from myelin containing tissue, which process consists essentially of the following steps:

extracting the myelin basic protein from the myelin containing tissue with an organic solvent selected from the group consisting of chloroform and compounds having a polarity similar to that of chloroform to produce an organic phase containing myelin basic protein;

incubating the organic phase in a mixture with a lower aliphatic alcohol or propylene glycol;

transferring the myelin basic protein from the mixture of the lower aliphatic alcohol or propylene glycol and organic solvent, to an aqueous phase containing hydrogen ions (protons); and recovering the purified myelin basic protein.

2. The process according to claim 1, wherein the myelin containing tissue is central nervous system tissue.

3. The process according to claim 1, wherein the myelin containing tissue is fresh or frozen.

4. The process according to claim 1, wherein the extraction from the myelin containing tissue is performed with chloroform.

5. The process according to claim 1, further including the step of washing wherein the organic phase is with neutral water.

6. The process according to claim 1, wherein the lower aliphatic alcohol is methanol.

7. The process according to claim 1, wherein the lower aliphatic alcohol is 2-propanol.

8. The process according to claim 1, wherein the extracting, incubating, and the transfer steps take place at room temperature.

9. The process according to claim 1, wherein the purified myelin basic protein is recovered by freeze-drying.

10. The process according to claim 1, wherein the purified myelin basic protein is freeze-dried twice.

11. The process according to claim 1, wherein the purified myelin basic protein is recovered by gel filtration.

12. The process according to claim 2, wherein the myelin containing tissue is fresh or frozen.

* * * * *